US012636454B2

(12) United States Patent
Sandmore et al.

(10) Patent No.: US 12,636,454 B2
(45) Date of Patent: May 26, 2026

(54) MULTISTAGE EXPANDABLE LOADING DILATOR

(71) Applicant: Cook Medical Technologies LLC, Bloomington, IN (US)

(72) Inventors: Donald R. Sandmore, Ellettsville, IN (US); Erin Roberts, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 931 days.

(21) Appl. No.: 17/864,111

(22) Filed: Jul. 13, 2022

(65) Prior Publication Data

US 2023/0032980 A1 Feb. 2, 2023

Related U.S. Application Data

(60) Provisional application No. 63/227,030, filed on Jul. 29, 2021.

(51) Int. Cl.
A61M 16/04 (2006.01)
A61B 17/34 (2006.01)

(52) U.S. Cl.
CPC ...... A61M 16/049 (2014.02); A61M 16/0472 (2013.01); A61B 2017/3486 (2013.01)

(58) Field of Classification Search
CPC ............ A61M 16/0429; A61M 16/049; A61M 16/0427; A61M 16/0479; A61M 16/0472; A61M 2025/0024; A61M 2025/0681; A61M 25/01; A61M 25/0014; A61M 29/00; A61B 17/3415; A61B 17/3439
See application file for complete search history.

(56) References Cited

U.S. PATENT DOCUMENTS

| | | | |
|---|---|---|---|
| 4,921,479 A | 5/1990 | Grayzel et al. | |
| 5,824,002 A | 10/1998 | Gentelia et al. | |
| 6,030,364 A | 2/2000 | Durgin et al. | |
| 6,637,435 B2 | 10/2003 | Ciaglia et al. | |
| 8,424,534 B2 | 4/2013 | Lyons et al. | |
| 9,089,663 B2 | 7/2015 | Rosenbaum et al. | |
| 9,555,206 B1 * | 1/2017 | Raimondi | A61M 16/0472 |
| 9,744,334 B2 | 8/2017 | Lahme et al. | |
| 9,775,643 B2 | 10/2017 | Leeflang et al. | |
| 9,808,598 B2 | 11/2017 | Korkuch et al. | |
| 10,398,469 B2 | 9/2019 | Coyle et al. | |

(Continued)

FOREIGN PATENT DOCUMENTS

WO WO2002083013 A1 10/2002

*Primary Examiner* — Colin W Stuart
*Assistant Examiner* — Douglas Y Sul
(74) *Attorney, Agent, or Firm* — Crowell & Moring LLP

(57) ABSTRACT

A loading dilator may include a first portion and a second portion. The first portion may include a first proximal end, a first distal end, and a first outer surface extending between the first proximal end and the first distal end. The second portion may include a second proximal end, a second distal end, and a second outer surface extending between the second proximal end and the second distal end. The first outer surface may include a plurality of slits extending along at least a portion of the length of the first portion. The plurality of slits may be spaced apart circumferentially around a longitudinal axis of the first portion. The length of the second portion may be smaller than the length of the first portion.

13 Claims, 3 Drawing Sheets

(56) References Cited

U.S. PATENT DOCUMENTS

| | | | |
|---|---|---|---|
| 10,537,718 B2 | 1/2020 | Lederman et al. | |
| 11,559,325 B2 * | 1/2023 | Pigott ............ | A61B 17/320725 |
| 2013/0025588 A1 * | 1/2013 | Bosel ................ | A61M 16/0488 |
| | | | 128/200.26 |
| 2014/0046357 A1 | 2/2014 | Neoh | |
| 2015/0246211 A1 * | 9/2015 | Bunch ............... | A61M 25/0074 |
| | | | 128/200.26 |
| 2018/0200478 A1 * | 7/2018 | Lorenzo ............ | A61M 25/0023 |
| 2019/0030294 A1 | 1/2019 | Mclaughlin et al. | |
| 2021/0322700 A1 * | 10/2021 | Gravenstein ...... | A61M 16/0488 |

* cited by examiner

FIG. 4

MULTISTAGE EXPANDABLE LOADING DILATOR

CROSS-REFERENCE TO RELATED APPLICATIONS

This application claims priority from U.S. Provisional Application No. 63/227,030, filed Jul. 29, 2021, the entirety of which is hereby fully incorporated by reference herein.

BACKGROUND

The present embodiments relate generally to medical devices, and more particularly, to medical devices for providing a passageway into a body opening.

There are several instances in which it may become desirable to provide a passageway into a body opening. For example, in order to provide an adequate air passageway to maintain the ability of a seriously ill or injured patient to breathe, an opening may be formed through the tracheal wall, and a tracheostomy tube may be inserted through the opening. Several methods and devices are known for forming, or enlarging, an opening in a tracheal wall. In one such method, a scalpel is used to form a small opening in the tracheal wall. A needle is inserted through the small opening, such that the tip of the needle is in the interior space of the trachea. A wire guide is then passed into the trachea through a bore in the needle, and the needle is thereafter withdrawn. Sequentially sized dilators are then advanced over the wire guide to facilitate gradual dilation of the tracheal entrance to an appropriate size.

Following formation of the opening, loading dilators are used in the placement of tracheostomy tubes. To pass a tracheostomy tube through the opening, a loading dilator is pre-loaded with the tracheostomy tube (forming a loading dilator/tracheostomy tube combination), and the distal end portion of the combination is passed through the opening over the previously inserted wire guide. It is desirable to provide a loading dilator/tracheostomy tube combination that has a generally smooth transition from the loading dilator to the tracheostomy tube, thereby facilitating entry of the distal end portion of the combination through the opening. Tracheostomy tubes may be provided with various sizes and designs, and thus loading dilators may also be provided with various sizes and designs to accommodate correspondingly sized/designed tracheostomy tubes.

SUMMARY

One general aspect of the present disclosure includes a loading dilator, including a first portion including a first proximal end, a first distal end, and a first outer surface extending between the first proximal end and the first distal end; and a second portion including a second proximal end, a second distal end, and a second outer surface extending between the second proximal end and the second distal end, where the first outer surface includes a plurality of slits extending along at least a portion of the length of the first portion, where the plurality of slits are spaced apart circumferentially around a longitudinal axis of the first portion, and where the length of the second portion is smaller than the length of the first portion.

Another general aspect of the present disclosure includes a system for providing a passageway into a body opening, including a tubular member including an inner lumen extending through the tubular member; and a loading dilator including a first portion, a second portion, and a main lumen extending through the first portion and the second portion, where the first portion of the loading dilator is configured to transition between a relaxed state with a smaller diameter and a plurality of expanded states with a plurality of varying larger diameters, where the inner lumen of the tubular member is configured to slidably receive the loading dilator when the first portion of the loading dilator is the relaxed state, and where at least a portion of the tubular member and the loading dilator form a snug engagement therebetween when the first portion of the loading dilator is in one of the plurality of expanded states.

Another general aspect of the present disclosure includes a method of positioning a tubular member across a body opening, including inserting a loading dilator through an inner lumen of the tubular member, the loading dilator including a first portion, a second portion, and a main lumen extending through the first portion and the second portion; inserting a support member into the main lumen of the loading dilator until at least a part of the first portion of the loading dilator is expanded into a snug engagement with an inner surface of the tubular member; introducing a distal end of the second portion of the loading dilator into the opening; advancing the tubular member, the loading dilator, and the support member as a unit into the opening until the tubular member is properly positioned; and removing the loading dilator and the support member from the tubular member.

Other systems, methods, features and advantages of the invention will be, or will become, apparent to one with skill in the art upon examination of the following figures and detailed description. It is intended that all such additional systems, methods, features and advantages be within the scope of the invention.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 4 is a schematic side view of a system for providing a passageway into a body opening according to an embodiment of the present invention, showing a tubular member extending over at least a portion of the loading dilator of FIG. 1 and the loading dilator of FIG. 1 extending over at least a portion of a support member.

DETAILED DESCRIPTION OF THE PREFERRED EMBODIMENT

In the present application, the term "proximal" refers to a direction that is generally towards a physician during a medical procedure, while the term "distal" refers to a direction that is generally towards a target site within a patient's anatomy during a medical procedure.

Figures 1, 1A:
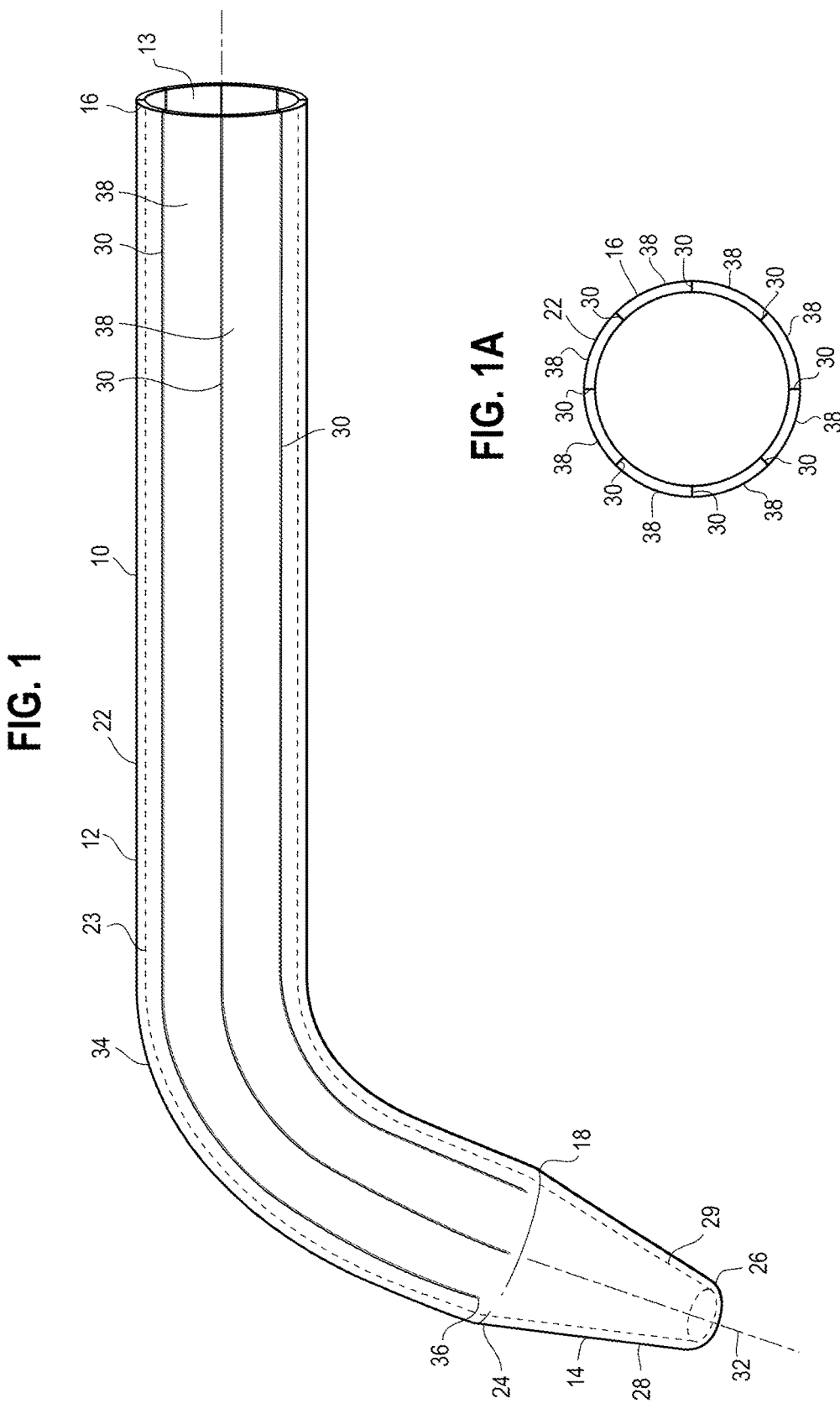
FIG. 1 is a schematic side view of a loading dilator according to an embodiment of the present invention, including a first portion and a second portion and extending between a first proximal end of the first portion and a second distal end of the second portion.
FIG. 1A is a schematic end view of the first proximal end of the first portion of the loading dilator of FIG. 1, showing the first portion with a plurality of slits in a relaxed state.

Referring to FIGS. 1-4, an embodiment of a loading dilator 10 and a system 20 for providing a passageway into a body opening using the loading dilator 10 are shown. As shown in FIG. 1, the loading dilator 10 includes a first portion 12, a second portion 14, and a main lumen 13 extending through the first portion 12 and the second portion 14. The first portion includes a first proximal end 16, a first distal end 18, and a first outer surface 22 and a first inner surface 23 extending between the first proximal end 16 and the first distal end 18. The second portion 14 includes a second proximal end 24, a second distal end 26, and a second outer surface 28 and a second inner surface 29 extending between the second proximal end 24 and the second distal end 26. The second portion 14 extends distally from the first distal end 18 of the first portion 12, where the first portion 12 and the second portion 14 may be integrally formed or connected together through any possible means. The length of the second portion 14 may be smaller than the length of the first portion 12.

Figure 2:
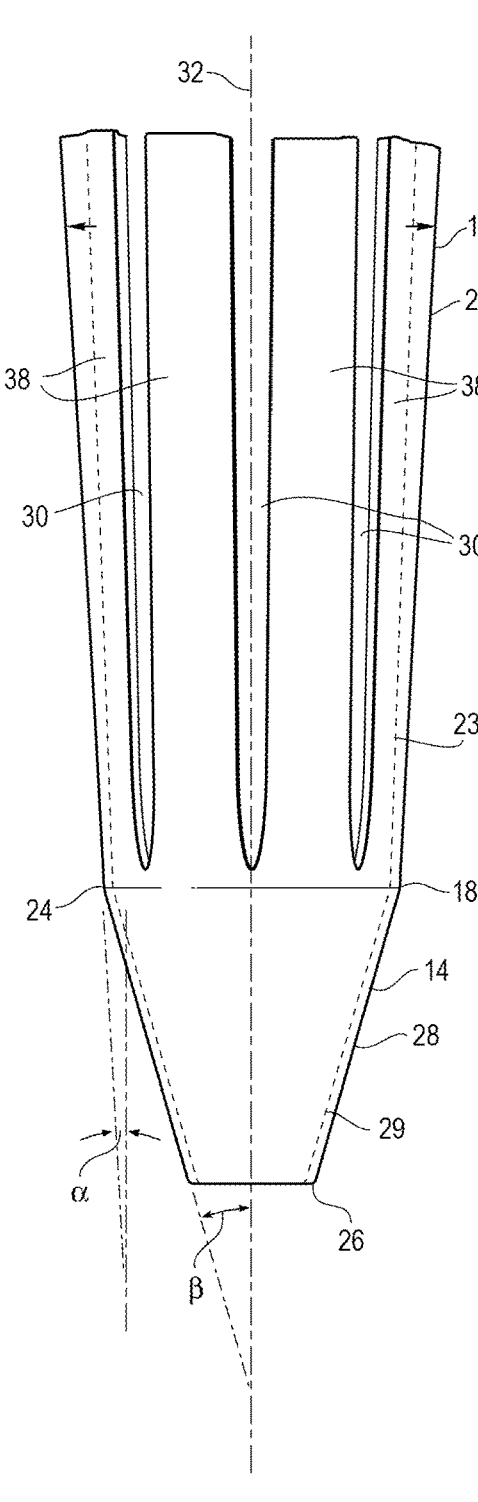
FIG. 2 is a partially enlarged schematic side view of a portion of the loading dilator of FIG. 1, showing the first portion with a plurality of slits in an expanded state.

As shown in FIG. 1, the first portion 12 may have an elongated tubular configuration. In some embodiments, the first portion 12 may be substantially straight in a default state (e.g., when no force is applied thereon), and is flexible enough to bend to match with other component angles while still performing the intended functions discussed in greater detail below. In some embodiments, the first portion 12 may be in a bent configuration in a default state (e.g., when no force is applied thereon), where the pre-bent angle aids in proper insertion of the total assembly including another tubular member (e.g., a tracheostomy tube). For example, as shown in FIG. 1, the first portion 12 includes a curved section 34. The longitudinal axis 32 of the first portion 12 may extend along the same line of the longitudinal axis of the loading dilator 10. The second outer surface 28 of the second portion 14 may be tapered for ease of entry into a body opening, as discussed in greater detail below. As shown in FIGS. 1 and 2, the second outer surface 28 of the second portion 14 may have a second taper, tapering from a larger diameter at the second proximal end 24 to a smaller diameter at the second distal end 26. In some embodiments, the first outer surface 22 of the first portion 12 may have a first taper, tapering from a larger diameter at the first proximal end 16 to a smaller diameter at the first distal end 18.

In some embodiments, the first taper may be less sharp relative to the longitudinal axis 32 of the loading dilator 10 than the second taper. As shown in FIG. 2, the first taper of the first outer surface 22 may form a first angle $\alpha$ relative to the longitudinal axis 32 of the loading dilator 10, and the second taper of the second outer surface 28 may form a second angle $\beta$ relative to the longitudinal axis 32. The degrees of the first angle $\alpha$ and the second angle $\beta$ may be varied, as desired and/or needed, without departing from the scope of the present invention. For example, the first angle $\alpha$ may deviate about 5 to about 25 degrees from the longitudinal axis 32, and the second angle $\beta$ may deviate about 20 to about 45 degrees from the longitudinal axis 32. The term "about" is specifically defined herein to include the specific value referenced as well as a dimension that is within 5% of the dimension both above and below the dimension.

Figure 3:
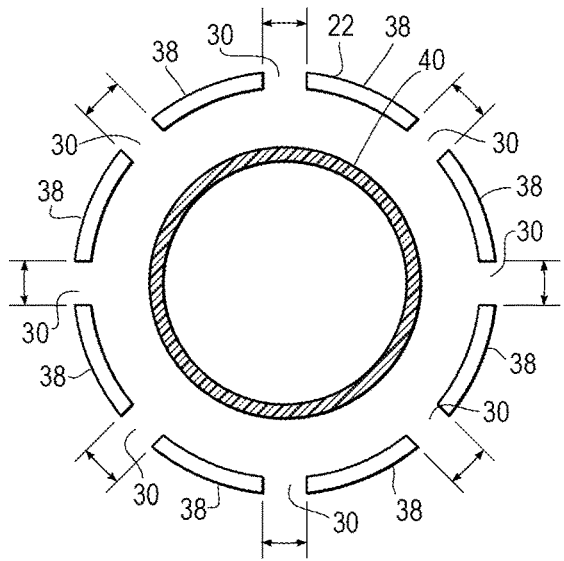
FIG. 3 is a partially enlarged schematic end view of the first proximal end of the first portion of the loading dilator of FIG. 1, showing a support member inserted into a main lumen of the loading dilator and the first portion of the loading dilator with a plurality of slits in an expanded state.

The first portion 12 may be expandable. In some embodiments, the first outer surface 22 may include a plurality of slits 30 extending along at least a portion of the length of the first portion 12. For example, as shown in FIG. 1, the first outer surface 22 includes a plurality of slits 30 extending along a length of the first portion 12 from the first proximal end 16 to a distal end 36 of the plurality of slits 30, where the distal end 36 of the plurality of slits 30 is proximal of the first distal end 18 of the first portion 12. In some embodiments, as shown in FIGS. 1, 1A, and 3, the plurality of slits 30 may be spaced apart circumferentially around the longitudinal axis 32 of the first portion 12. In FIGS. 1A and 3, the plurality of slits 30 include eight slits spaced equidistant apart circumferentially around the longitudinal axis 32 of the first portion 12. It will be appreciated that the configuration (e.g., size, shape) of the slits 30, the number of the slits 30, and the distance they are spaced apart may be varied, as desired and/or needed, without departing from the scope of the present invention. The second portion 14 may be solid, where the second outer surface 28 of the second portion 14 does not have slits and are not expandable. A solid second portion 14 is advantageous for facilitating securing a wire guide and/or a catheter extending through the main lumen 13 of the loading dilator 10.

In some embodiments, the first outer surface 22 may include a plurality of leaves 38 that are at least partially spaced apart by the plurality of slits 30. For example, as shown in FIGS. 1 and 2, the plurality of leaves 38 may extend distally along a length of the first portion 12 from the first proximal end 16 of the first portion 12 and be connected at the first distal end 18 of the first portion 12. As shown in FIGS. 2 and 3, the plurality of leaves 38 are configured to expand radially outwardly when the plurality of slits 30 are stretched apart (e.g., by insertion of a support member 40 into the main lumen 13 of the loading dilator 10, as discussed in greater detail below). With this configuration, the first portion 12 of the loading dilator 10 is configured to transition between a relaxed state with a smaller diameter (e.g., when the plurality of slits 30 are not stretched apart, as shown in FIG. 1A) and an expanded state with a larger diameter (e.g., when the plurality of slits 30 are stretched apart, as shown in FIGS. 2 and 3). In some embodiments, the first portion 12 of the loading dilator 10 is configured to transition between a relaxed state with a smaller diameter and a plurality of expanded states with a plurality of varying larger diameters (e.g., by insertion of a support member 40, as discussed in greater detail below). The first portion 12 of the loading dilator 10 is configured to transition back towards the relaxed state when the support member 40 is removed from the main lumen 13 of the loading dilator 10.

Figure 4:
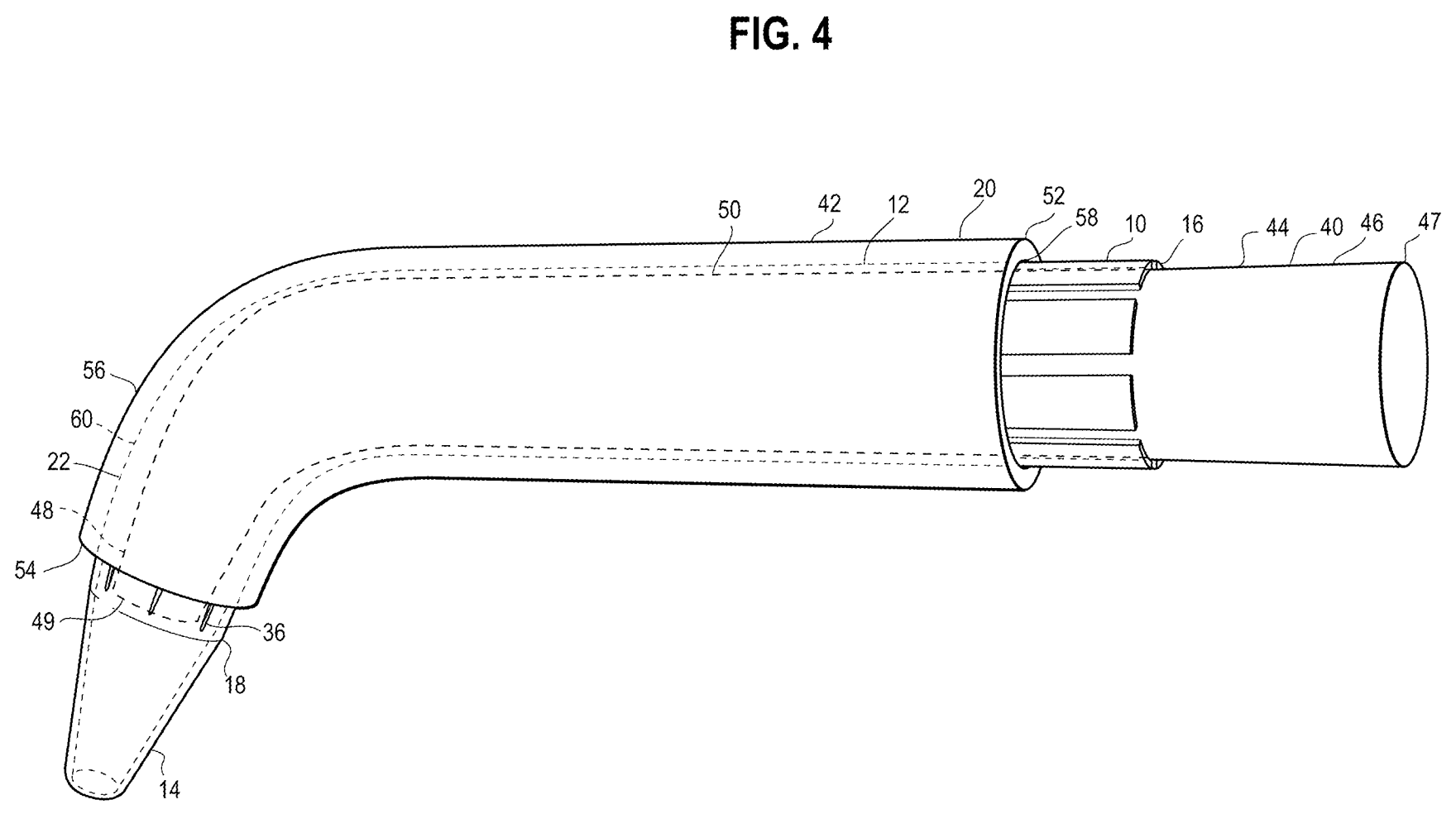

In some embodiments, the loading dilator 10 may be used in conjunction with other devices to provide a passageway into a body opening. Referring to FIG. 4, for example, a system 20 for providing a passageway into a body opening is shown. The system 20 includes a loading dilator 10, a support member 40, and a tubular member 42. The loading dilator 10 may be used for inserting the tubular member 42 across an opening formed through a body wall such that a passageway into the body opening may be established by the tubular member 42. The support member 40 may be used to transition the loading dilator 10 into a plurality of expanded states with a plurality of varying larger diameters to accommodate a plurality of tubular members 42 with various configurations (e.g., varying diameters).

One non-limiting example of such use is the insertion of a tracheostomy tube across an opening formed through the tracheal wall. Tracheostomy tubes may be provided in a variety of different diameters. It would be desirable to provide a loading dilator that can be configured to accommodate tracheostomy tubes having a range of diameters, and that can be configured to minimize the transition between the loading dilator and the tracheostomy tube upon insertion of the loading dilator into the tracheostomy tube to ease entry of the loading dilator/tracheostomy tube combination into the opening formed in the tracheal wall. It will be appreciated that the loading dilator 10 and the system 20 may also be used in other medical procedures, without departing from the scope of the present invention.

The support member 40 is configured to extend through at least a portion of the main lumen 13 of the loading dilator 10 to transition the first portion 12 of the loading dilator 10 from a relaxed state with a smaller diameter to a plurality of expanded states with a plurality of varying larger diameters. In some embodiments, as shown in FIG. 4, the support member 40 includes an elongated body 44 having a proximal end portion 46 and a distal end portion 48. The proximal end portion 46 extends to a proximal end 47, and the distal end portion 48 extends to a distal end 49. The distal end portion 48 may be curved and/or tapered to facilitate engagement with the first portion 12 of the loading dilator 10.

The diameter of at least a portion of the outer surface 50 of the support member 40 may increase in a distal to proximal longitudinal direction. In some embodiments, the diameter of the outer surface 50 at the distal end 49 of the support member 40 may be smaller than the diameter of the first inner surface 23 of the first portion 12 of the loading dilator 10 at the first proximal end 16 and larger than the diameter of the first inner surface 23 of the first portion 12 at the first distal end 18, when the first portion 12 is in a relaxed state. With this configuration, as the distal end 49 of the support member 40 extends distally in the main lumen 13 of the loading dilator 10 from the first proximal end 16, the outer surface 50 at the distal end 49 of the support member 40 will hit the first inner surface 23 of the first portion 12. Then, as the support member 40 continues to extend distally, the plurality of slits 30 will be stretched apart by the support member 40, such that the first portion 12 of the loading dilator 10 is transitioned to an expanded state, as discussed above.

When the increasingly larger diameter of the outer surface 50 of the support member 40 extends distally in the main lumen 13 of the loading dilator 10, the first portion 12 may be transitioned to a plurality of expanded states with a plurality of varying larger diameters, depending on the diameter of the outer surface 50 of the support member 40 and the extent of insertion of the support member 40 in the main lumen 13. It will be appreciated that the diameter of the outer surface 50 of the support member 40 may be varied, as desired and/or needed, without departing from the scope of the present invention, as long as the insertion of the support member 40 in the main lumen 13 of the loading dilator 10 can transition the first portion 12 of the loading dilator 10 into desired/needed expanded states to be able to form a snug engagement between at least a portion of the first portion 12 of the loading dilator 10 and tubular members 40 with varying diameters, as discussed in greater detail below.

Referring to FIG. 4, the tubular member 42 may have a generally curved body, including a proximal end 52, a distal end 54, an outer surface 56 and an inner surface 60 extending between the proximal end 52 and the distal end 54, and an inner lumen 58 extending through the tubular member 42. The inner lumen 58 of the tubular member 42 is configured to slidably receive the loading dilator 10 when the first portion 12 of the loading dilator 10 is in a relaxed state. It will be appreciated that the diameter of the first outer surface

22 and the second outer surface 28 of the loading dilator 10 may be varied, as desired and/or needed, without departing from the scope of the present invention, as long as the loading dilator 10 can be slidably received in the inner lumen 58 of the tubular member 42 when the first portion 12 of the loading dilator 10 is in a relaxed state (e.g., including situations where lubrication is provided to aid in the insertion of the loading dilator 10 into the inner lumen 58 of the tubular member 42).

Expansion of the loading dilator 10 by insertion of the support member 40 may cause the plurality of leaves 38 to push against at least a portion of the inner surface 60 of the tubular member 42. That is when the first portion 12 of the loading dilator 10 is in one of the plurality of expanded states, at least a portion of the tubular member 42 and the loading dilator 10 may form a snug engagement therebetween, such that the tubular member 42 is held in place over the loading dilator 10, allowing the loading dilator/tubular member combination to be inserted into a body opening as a unit, as discussed in greater detail below. The ability of transitioning a single loading dilator 10 into a plurality of expanded states with varying larger diameters is advantageous for reducing the number of loading dilators needed for inserting tubular members with varying sizes and designs across a body opening to establish a passageway therethrough, thereby reducing components that need to be manufactured and reducing waste. It may also reduce user confusion in figuring out the appropriate loading dilator to be used with a particular tubular member.

In some embodiments, as shown in FIG. 4, the tubular member 42, the loading dilator 10, and the support member 40 may be configured to extend co-axially with the tubular member 42 extending over at least a portion of the loading dilator 10 and the loading dilator 10 extending over at least a portion of the support member 40. In some embodiments, the first portion 12 of the loading dilator 10 has a first length, the tubular member 42 has a second length, and the first length may be greater than the second length (e.g., as shown in FIG. 4).

In some embodiments, as shown in FIG. 4, when a portion of the tubular member 42 and the loading dilator 10 form a snug engagement therebetween, the distal end 54 of the tubular member 42 may be positioned proximally of the distal end 36 of the plurality of slits 30, the proximal end 52 of the tubular member 42 may be positioned distally of the first proximal end 16 of the first portion 12 of the loading dilator 10, and the distal end 54 of the tubular member 42 may contact the first outer surface 22 of the first portion 12 of the loading dilator 10 and form a smooth transition therebetween. This configuration is advantageous in that the tubular member 42 can be held in place over the loading dilator 10 with a smooth transition therebetween. The smooth transition formed between the expanded first outer surface 22 of the first portion 12 of the loading dilator 10 and the distal end 54 of the tubular member 42 is advantageous for easing entry of the loading dilator/tubular member combination through the body opening. As a result, the trauma experienced by the patient upon insertion of the loading dilator/tubular member combination through the body opening will be minimized.

In use, to position the tubular member 42 across a body opening to establish a passageway through the body opening, a user may insert a loading dilator 10 through the inner lumen 58 of the tubular member 42 until at least a portion of the plurality of slits 30 of the loading dilator 10 extends beyond the distal end 54 of the tubular member 42, where the loading dilator 10 is in a relaxed state with a smaller diameter. Then the user may insert (e.g., distally; without the need of using lubrication) a support member 40 into the main lumen 13 of the loading dilator 10 until at least a part of the first portion 12 of the loading dilator 10 is expanded into a snug engagement with the inner surface 60 of the tubular member 42 (e.g., the insertion of the support member 40 at least partially stretches apart the plurality of slits 30 and expands the plurality of leaves 38 into a snug engagement with the inner surface 60 of the tubular member 42), such that the tubular member 42 is held in place over the loading dilator 10, forming a unit of the tubular member 42, the loading dilator 10, and the support member 40. In some embodiments, the user may insert (e.g., distally) a support member 40 into the main lumen 13 of the loading dilator 10 until at least a part of the first portion 12 of the loading dilator 10 is expanded into a snug engagement with the inner surface 60 at the distal end 54 of the tubular member 42 and a smooth transition is formed between the loading dilator 10 and the tubular member 42 at the distal end 54 of the tubular member 42.

The user may then introduce the second distal end 26 of the second portion 14 of the loading dilator 10 into the body opening. Then, the user may advance the tubular member 42, the loading dilator 10, and the support member 40 as a unit into the opening until the tubular member 42 is properly positioned (e.g., at a desired depth/site). Then, the user may remove the loading dilator 10 and the support member 40 from the tubular member 42, leaving the tubular member 42 in place across the body opening. To remove the loading dilator 10 and the support member 40, the user may first retract proximally the support member 40 away from the loading dilator 10 to collapse the loading dilator 10 such that the tubular member 42 is disengaged from the loading dilator 10, and then the user may retract proximally the loading dilator 10 away from the tubular member 42.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A system for providing a passageway into a body opening, comprising:
    a tubular member including an inner lumen extending through the tubular member; and
    a loading dilator including a first portion, a second portion, and a main lumen extending through the first portion and the second portion,
    wherein the first portion of the loading dilator is configured to transition between a relaxed state with a smaller diameter and a plurality of expanded states with a plurality of varying larger diameters,
    wherein the inner lumen of the tubular member is configured to slidably receive the loading dilator when the first portion of the loading dilator is the relaxed state,
    wherein at least a portion of the tubular member and the loading dilator form a snug engagement therebetween when the first portion of the loading dilator is in one of the plurality of expanded states, and
    wherein the first portion of the loading dilator has a first length, the tubular member has a second length, and the first length is greater than the second length.

2. The system of claim 1, wherein the second portion of the loading dilator is not expandable.

3. The system of claim 1, further comprising a support member configured to extend through at least a portion of the main lumen of the loading dilator to transition the first portion of the loading dilator from the relaxed state to the plurality of expanded states.

4. The system of claim 3, wherein the tubular member, the loading dilator, and the support member are configured to extend co-axially with the tubular member extending over at least a portion of the loading dilator and the loading dilator extending over at least a portion of the support member.

5. The system of claim 3, wherein the first portion of the loading dilator is configured to transition back towards the relaxed state when the support member is removed from the main lumen of the loading dilator.

6. The system of claim 1, wherein the first portion of the loading dilator includes a plurality of slits extending along a length of the first portion, wherein a distal end of the tubular member is positioned proximally of distal ends of the plurality of slits and a proximal end of the tubular member is positioned distally of a first proximal end of the first portion of the loading dilator.

7. The system of claim 1, wherein the first portion of the loading dilator includes a first proximal end, a first distal end, and a first outer surface extending between the first proximal end and the first distal end,
    wherein the first outer surface includes a plurality of slits extending along a length of the first portion from the first proximal end to a distal end of the plurality of slits, and
    wherein the distal end of the plurality of slits is proximal of the first distal end of the first portion.

8. The system of claim 7, wherein the first outer surface includes a plurality of leaves that are at least partially spaced apart by the plurality of slits, and wherein the plurality of leaves are configured to expand radially outwardly when the plurality of slits are stretched apart.

9. The system of claim 7, wherein the tubular member includes a proximal end, a distal end, and an outer surface extending between the proximal end and the distal end, and
    wherein when a portion of the tubular member and the loading dilator form a snug engagement therebetween, the distal end of the tubular member is positioned proximally of the distal end of the plurality of slits and the proximal end of the tubular member is positioned distally of the first proximal end of the first portion of the loading dilator.

10. The system of claim 9, wherein when a portion of the tubular member and the loading dilator form a snug engagement therebetween, the distal end of the tubular member contacts the first outer surface of the first portion of the loading dilator and forms a smooth transition therebetween.

11. A method of positioning a tubular member across a body opening, comprising:
    inserting a loading dilator through an inner lumen of the tubular member, the loading dilator including a first portion, a second portion, and a main lumen extending through the first portion and the second portion, wherein the first portion of the loading dilator includes a plurality of slits extending along at least a portion of a length of the first portion;
    inserting a support member into the main lumen of the loading dilator until at least a part of the first portion of the loading dilator is expanded into a snug engagement with an inner surface of the tubular member, such that a distal end of the tubular member is positioned proximally of distal ends of the plurality of slits and a proximal end of the tubular member is positioned distally of a first proximal end of the first portion of the loading dilator;

introducing a distal end of the second portion of the loading dilator into the opening;

advancing the tubular member, the loading dilator, and the support member as a unit into the opening until the tubular member is properly positioned; and removing the loading dilator and the support member from the tubular member.

12. The method of claim 11, wherein removing the loading dilator and the support member from the tubular member further comprises:

retracting proximally the support member away from the loading dilator to collapse the loading dilator such that the tubular member is disengaged from the loading dilator; and retracting proximally the loading dilator away from the tubular member.

13. The method of claim 11, wherein the first portion of the loading dilator includes a plurality of leaves that are at least partially spaced apart by the plurality of slits, and wherein inserting the support member into the main lumen of the loading dilator further comprises at least partially stretching apart the plurality of slits and expanding the plurality of leaves into a snug engagement with the inner surface of the tubular member.

\*   \*   \*   \*   \*